(12) United States Patent
Diehl et al.

(10) Patent No.: US 9,034,905 B2
(45) Date of Patent: May 19, 2015

(54) SYNERGISTIC MICROBICIDAL COMBINATIONS

(75) Inventors: Megan Anne Diehl, Line Lexington, PA (US); Eileen Fleck Warwick, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 1850 days.

(21) Appl. No.: 10/665,343

(22) Filed: Sep. 18, 2003

(65) Prior Publication Data

US 2004/0152748 A1 Aug. 5, 2004

Related U.S. Application Data

(60) Provisional application No. 60/445,122, filed on Feb. 5, 2003.

(51) Int. Cl.
*A61K 31/425* (2006.01)
*A61K 31/192* (2006.01)
*A61K 31/4164* (2006.01)

(52) U.S. Cl.
CPC ............ *A61K 31/425* (2013.01); *A61K 31/192* (2013.01); *A61K 31/4164* (2013.01)

(58) Field of Classification Search
USPC .......................... 514/372, 373, 389, 519, 569
See application file for complete search history.

(56) References Cited

U.S. PATENT DOCUMENTS

| | | | |
|---|---|---|---|
| 4,105,431 A * | 8/1978 | Lewis et al. ................ 504/156 | |
| 5,037,989 A | 8/1991 | Willingham et al. | |
| 5,342,784 A | 8/1994 | Yamada et al. | |
| 5,424,324 A | 6/1995 | Willingham | |
| 5,489,588 A * | 2/1996 | Hsu .......................... 514/237.8 | |
| 5,591,759 A | 1/1997 | Ito et al. | |
| 5,599,827 A | 2/1997 | Gironda | |
| 6,114,366 A | 9/2000 | Lutz et al. | |
| 6,121,302 A | 9/2000 | Rothenburger et al. | |
| 6,146,645 A * | 11/2000 | Deckers et al. ............... 424/401 | |
| 6,159,999 A | 12/2000 | Yagi et al. | |
| 6,211,213 B1 | 4/2001 | El A'mma | |
| 6,255,331 B1 | 7/2001 | El A'mma et al. | |
| 6,361,788 B1 | 3/2002 | Antoni-Zimmermann et al. | |
| 6,410,039 B1 | 6/2002 | Walker | |
| 6,417,211 B1 | 7/2002 | Petigard et al. | |
| 6,511,673 B1 * | 1/2003 | Chia et al. ..................... 424/401 | |
| 6,706,526 B2 * | 3/2004 | Lang et al. ..................... 436/18 | |
| 2004/0091558 A1 * | 5/2004 | Lutz et al. ..................... 424/745 | |
| 2008/0227766 A1 * | 9/2008 | Wunder et al. ................ 514/186 | |
| 2009/0175966 A1 * | 7/2009 | Lutz et al. ..................... 424/739 | |
| 2009/0191289 A1 * | 7/2009 | Lutz et al. ..................... 424/739 | |
| 2013/0064899 A1 * | 3/2013 | Schmidt et al. ............... 424/618 | |

FOREIGN PATENT DOCUMENTS

| | | |
|---|---|---|
| DE | 19534532 | 3/1997 |
| EP | 0773281 | 5/1997 |
| EP | 124153 | * 10/2002 |
| GB | 2138799 | 10/1984 |
| JP | 4270203 | 9/1992 |
| WO | 01/00022 | 1/2001 |
| WO | 01/50855 | 7/2001 |
| WO | 02/17716 | 3/2002 |

OTHER PUBLICATIONS

BPAI Decision Affirmed (Appeal 2008-5426, U.S. Appl. No. 10/665,343, decided: Nov. 21, 2008).*
Krebs, H.A., Wiggins, D., Stubbs, M., Sols, A., and Bedoya, F. 1983. Studies on the mechanism of the antifungal action of benzoate. Biochem. J. 214:657-663.
Russell, A.D., Hugo W.B., and Ayliffe, G.A.J. 1999. Principles and Practice of Disinfection, Preservation and Sterilization. Third Edition. Blackwell Science, London. pp. 21-25, 155-161, 272-273, 491-492, 504-506, 803.
Lueck, S. 1980. Benzoic acid. In: Antimicrobial Food Preservatives. Springer Verlag, Berlin. pp. 210-218.
Krebs, H.A., Wiggins, D., Stubbs, M., Sols, A. and Bedoya, F. 1983. Studies on the mechanism of the antifungal action of benzoate. Biochem. J. 214:657-663.
Russell, A.D., Hugo W.B., and Ayliffe, G.A.J. 1999. Principles and Practice of Disinfection, Preservation and Sterilization. Third Edition. Blackwell Science, London. pp. Cover, Legals, 21-25, 155-161, 272-273, 491-492, 504-506, 803.
Lueck, E. 1980. Benzoic acid, In: Antimicrobial Food Additives. Springer Verlag, Berlin. pp. Cover, Legals, 210-218.

* cited by examiner

*Primary Examiner* — Sabiha N Qazi
(74) *Attorney, Agent, or Firm* — The Dobrusin Law Firm, PC

(57) ABSTRACT

Antimicrobial compositions based on the synergistic combination of 2-methyl-3-isothiazolone and selected commercial microbicides where the compositions are substantially free of halogenated 3-isothiazolone, are disclosed. Particularly preferred are combinations of 2-methyl-3-isothiazolone together with benzoic acid, citric acid, sorbic acid, 1,2-dibromo-2,4-dicyanobutane, 1,3-dimethylol-5,5-dimethylhydantoin, phenoxyethanol, benzyl alcohol, zinc pyrithione or climbazole, that provide enhanced microbicidal efficacy at a combined active ingredient level lower than that of the combined individual 3-isothiazolone and commercial microbicide effective use levels.

1 Claim, No Drawings

SYNERGISTIC MICROBICIDAL COMBINATIONS

CROSS REFERENCE TO RELATED PATENT APPLICATIONS

This is a non-provisional application of U.S. provisional application Ser. No. 60/445,122 filed Feb. 5, 2003.

BACKGROUND

This invention relates to synergistic microbicidal combinations and, in particular, to synergistic microbicidal combinations of 2-methyl-3-isothiazolone with one or more selected commercial microbicides, where the resulting composition is substantially free of halogenated 3-isothiazolone. Kathon™ CG biocide (3/1 ratio of 5-chloro-2-methyl-3-isothiazolone to 2-methyl-3-isothiazolone) and Neolone™ 950 bactericide (2-methyl-3-isothiazolone) are highly effective preservatives and may be used in combination with a variety of commercially available preservatives to prevent microbial contamination in personal care applications, such as cosmetics and toiletries (see "Kathon™ CG Cosmetic and Toiletry Preservative" Bulletin CS-663, September 1997, and "Neolone™ 950 Preservative for Personal Care" Bulletin CS-707, May 2001, Rohm and Haas Company, Philadelphia, Pa.). U.S. Pat. No. 5,591,759 discloses the use of 1,2-dibromo-2,4-dicyanobutane to stabilize isothiazolone mixtures of 5-chloro-2-methyl-3-isothiazolone/2-methyl-3-isothiazolone (9/1 ratio). Patent application WO 01/50855 discloses preservative formulations for extending the lifetime of cut flowers based on preservative formulations containing acrylic copolymer additives, saccharide derivatives and antimicrobial mixtures, including those based on 2-methyl-3-isothiazolone in the presence of citric acid/citrates.

Many other microbicidal agents are known. These are commercially available for the control of microorganisms in a variety of loci. Sometimes, many microbicides cannot provide effective antimicrobial control even at high use concentrations due to weak activity against certain microorganisms. Without effective microorganism control, loss of product, inferior product, production time loss, health hazard and other problems may occur in the locus treated. There is a need for a method to control various microorganisms that does not rely on high use levels of combinations of different microbicidal agents, but still provides effective overall control of the microorganisms that is both quick and long lasting.

The problem addressed by the present invention is to overcome deficiencies of previous microbicide combinations by providing a combination of microbicidal agents that is more effective than the individual microbicides used alone and that can be used at lower overall levels while providing efficacy similar to the original individual microbicide levels.

STATEMENT OF INVENTION

The present invention provides a microbicidal composition comprising a synergistic mixture, the first component of which is 2-methyl-3-isothiazolone, and the second component of which is one or more commercial microbicides selected from the group consisting of benzoic acid, sorbic acid, 1,2-dibromo-2,4-dicyanobutane, 1,3-dimethylol-5,5-dimethylhydantoin, phenoxyethanol, zinc pyrithione and climbazole; wherein the ratio of the first component to the second component is from 1/0.001 to 1/1000; and wherein the composition is substantially free of halogenated 3-isothiazolone.

In another embodiment the present invention provides a microbicidal composition comprising a synergistic mixture, the first component of which is 2-methyl-3-isothiazolone, and the second component of which is one or more commercial microbicides selected from the group consisting of citric acid and benzyl alcohol; wherein the ratio of the first component to the second component is from 1/8 to 1/24 when the second component is citric acid; wherein the ratio of the first component to the second component is from 1/0.13 to 1/32 or from 1/80 to 1/1600 when the second component is benzyl alcohol; and wherein the composition is substantially free of halogenated 3-isothiazolone.

The present invention further provides a method of inhibiting the growth of microorganisms in a locus comprising introducing to, at or on, the locus a microorganism inhibiting amount of the aforementioned synergistic mixture; and wherein the amount of synergistic mixture is from 0.1 to 10,000 parts per million active ingredient.

In a preferred embodiment the present invention provides a method of inhibiting the growth of microorganisms as described above wherein the microorganisms are selected from one or more of bacterial and fungal microorganisms.

DETAILED DESCRIPTION

We have discovered that 2-methyl-3-isothiazolone (MI) may be combined with selected commercial microbicides to provide enhanced microbicidal efficacy at a combined active ingredient level lower than that of the combined individual 3-isothiazolone or commercial microbicide effective use levels, where the resulting composition is substantially free of halogenated 3-isothiazolone. Preferably the microbicidal compositions are also substantially free of metal salt stabilizers, such as nitrate or magnesium salts; these "salt-free" microbicidal compositions are especially useful to protect personal care compositions against microbial contamination.

It has been discovered that mixtures of MI with one or more of the commercial microbicides of the present invention in a ratio of 1/0.001 to 1/1000 result in synergistic microbicidal activities against a wide range of microorganisms. Synergy occurs when the disruptive interaction on the organisms treated by the two compounds together is greater than the sum of such interactions of both compounds when used alone. Such synergy does not arise from the expected activity of the components when added together.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, and MIC=minimum inhibitory concentration. Unless otherwise specified, ranges listed are to be read as inclusive and combinable, temperatures are in degrees centigrade (° C.), and references to percentages (%) are by weight. "Salt-free" means that the composition contains zero or up to 0.5%, preferably zero or up to 0.1%, and more preferably zero or up to 0.01%, of metal salt, based on weight of the composition.

The microbicidal compositions of the present invention are substantially free of halogenated 3-isothiazolone; that is, zero or up to 3%, preferably zero or up to 1% and more preferably zero or up to 0.5%, of halogenated 3-isothiazolone may be present, based on combined weight of halogenated 3-isothiazolone and 2-methyl-3-isothiazolone. Microbicidal compositions dependent on the presence of halogenated 3-isothiazolone are susceptible to chemical degradation and may require additional stabilizer components, such as the aforementioned metal salt stabilizers; salt stabilizers sometimes create unacceptable properties in finished formulations. For this reason it is desirable to provide microbicide formulations substantially free of halogenated 3-isothiazolone, but that still provide the degree of antimicrobial protection provided by the halogenated 3-isothiazolones; such are the microbicidal compositions of the present invention that are based on 2-methyl-3-isothiazolone, which do not require metal stabilizers.

MI may be used in the synergistic mixtures of the present invention "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials and charcoal. It is preferred that MI is formulated in water.

The second microbicide components of the combinations of the present invention are well-known and generally commercially available microbicides, and include benzoic acid, citric acid, sorbic acid, 1,2-dibromo-2,4-dicyanobutane, 1,3-dimethylol-5,5-dimethylhydantoin, phenoxyethanol, benzyl alcohol, zinc pyrithione and climbazole. The ratio of MI to the second microbicide component is typically from 1/0.001 to 1/1000, and preferably from 1/0.05 to 1/100. These microbicides may be used in the synergistic mixtures of the present invention "as is" or may first be formulated together with a suitable solvent, a solid carrier or as a dispersion. Suitable solvents and solid carriers are those described above for MI.

When a water-insoluble second microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

Any formulation of MI may be used with any formulation of the second microbicide component in the synergistic mixtures of the present invention. When both the MI and the second microbicide component are each first formulated with a solvent, the solvent used for MI may be the same as or different from the solvent used to formulate the other commercial microbicide. It is preferred that the two solvents are miscible. In the alternative, the MI and the other microbicide may be combined directly and then a solvent added to the mixture.

Those skilled in the art will recognize that the MI and the second microbicide component of the present invention may be added to a locus sequentially, simultaneously, or may be combined before being added to the locus. It is preferred that the MI and the second microbicide component be added to a locus simultaneously or combined prior to being added to the locus. When the microbicides are combined prior to being added to a locus, such combination may optionally contain adjuvants, such as, for example, solvent, thickeners, antifreeze agents, colorants, sequestrants (such as ethylenediamine-tetraacetic acid, ethylenediaminedisuccinic acid, iminodisuccinic acid and salts thereof), dispersants, surfactants, stabilizers, scale inhibitors and anti-corrosion additives.

The microbicidal compositions of the present invention can be used to inhibit the growth of microorganisms by introducing a microbicidally effective amount of the compositions onto, into, or at a locus subject to microbial attack. Suitable loci include, for example: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the microbicidal compositions of the present invention are used to inhibit the growth of microorganisms at a locus selected from one or more of emulsions, dispersions, paints, latexes, household products, cosmetics, toiletries, shampoos, soaps, detergents and industrial cleaners. In particular, the microbicidal compositions are useful in personal care applications, such as hair care (for example, shampoo and dyes) and skin care (for example, sunscreens, cosmetics, soaps, lotions and creams) formulations.

When the synergistic compositions of the present invention are used in personal care compositions, the formulated compositions may also comprise one or more ingredients selected from UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

Suitable UV radiation-absorbing agents (including chemical absorbers and physical blockers) include, for example, oxybenzone, dioxybenzone, sulisobenzone, menthyl anthranilate, para-aminobenzoic acid, amyl para-dimethylaminobenzoic acid, octyl para-dimethylaminobenzoate, ethyl 4-bis(hydroxypropyl)aminobenzoate, polyethylene glycol (PEG-25) para-aminobenzoate, diethanolamine para-methoxycinnamate, 2-ethoxyethyl para-methoxycinnamate, ethylhexyl para-methoxycinnamate, octyl para-methoxycinnamate, isoamyl para-methoxycinnamate, 2-ethylhexyl-2-cyano-3,3-diphenylacrylate, 2-ethylhexyl salicylate, homomenthyl salicylate, glyceryl aminobenzoate, triethanolamine salicylate, digalloyl trioleate, lawsone with dihydroxyacetone, 2-phenylbenzimidazole-5-sulfonic acid, 4-methylbenzylidine camphor, avobenzone, titanium dioxide and zinc oxide. Alternatively, UV radiation-absorbing agents such as triazines, benzotriazoles, vinyl group-containing amides, cinnamic acid amides and sulfonated benzimidazoles may also be used.

Suitable surfactants include, for example, nonionic, anionic, cationic and amphoteric surfactants and mixtures thereof; such as PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate and N-alkyl substituted lactam (such as N-octyl pyrrolidone).

Suitable thickeners or rheology modifiers include, for example, hydrophobically modified nonionic ethoxylated urethanes, polycarboxylic acid thickeners such as acrylates/steareth-20 methacrylate copolymer, carbomers, acrylates copolymer and acrylates $C_{10-30}$ alkyl acrylate crosspolymer.

The personal care compositions improved by the method of this invention include, for example:
(a) hair care formulations, including shampoos, hair dyes, hair conditioners, gels, mousses and hair sprays; and
(b) skin care and nail care formulations, including nail coatings, cosmetics, astringents, depilatories, facial make-up formulations, sunscreens and sunblocks, pre-moistened wipes, hand creams, hand and body soaps, and hand and body lotions.

The cosmetic formulations typically contain water, film forming materials, emulsifiers, softeners, emollients, oils, stabilizers, thickeners, neutralizers, perfume, colorants, pigments and combinations thereof. The sunscreen formulations typically contain UV radiation-absorbing agents, water, film forming materials, emulsifiers, emollients, waterproofing agents, oils, stabilizers, thickeners, preservatives, perfume, colorants, insecticides, humectants and combinations thereof.

Optionally, other additives, such as additional film forming agents, plasticizers, antifoaming agents, leveling aids, excipients, vitamins, natural extracts, proteins, sequestrants, dispersants, antioxidants, suspending agents and solvents may be added to the personal care formulations described above. Suitable solvents include, for example, $C_1$-$C_{12}$ straight or branched chain alcohols such as ethanol, isopropanol, or propanol; alkyl esters such as ethyl acetate; ketones; and combinations thereof.

The specific amount of the synergistic combinations necessary to inhibit or control the growth of microorganisms in a locus depends upon the particular compounds in the combination and particular locus to be protected. Typically, the amount of the synergistic combinations of the present invention to control the growth of microorganisms in a locus is sufficient if it provides from 0.1 to 10,000 ppm active ingredient of the synergistic mixture in the locus. It is preferred that the synergistic mixture be present in an amount of 0.5 to 5000 ppm, and more preferably from 1 to 3000 ppm, in the locus.

Microorganisms evaluated for effectiveness of control by the compositions of the present invention include bacterial (*P. aeruginosa* and *S. aureus*) and fungal (*A. niger* and *C. albicans*) microorganisms, in particular Gram (−) bacteria and Gram (+) bacteria, as well as yeast and mold.

Combinations of MI with sorbic acid, 1,2-dibromo-2,4-dicyanobutane, 1,3-dimethylol-5,5-dimethylhydantoin or phenoxyethanol were particulary effective against both Gram (−) and Gram (+) bacteria. Combinations of MI with benzoic acid, zinc pyrithione or benzyl alcohol were particulary effective against Gram (−) bacteria. Combinations of MI with citric acid or climbazole were particulary effective against Gram (+) bacteria. Combinations of MI with phenoxyethanol, zinc pyrithione or benzyl alcohol were particulary effective against both yeast and mold. Combinations of MI with benzoic acid, 1,2-dibromo-2,4-dicycanobutane or climbazole were particulary effective against yeast. Combinations of MI with sorbic acid were particulary effective against mold. Combinations of MI with benzoic acid, sorbic acid, 1,2-dibromo-2,4-dicycanobutane, phenoxyethanol, zinc pyrithione, climbazole or benzyl alcohol were effective against both bacterial and fungal microorganisms.

When benzoic acid is used in the synergistic mixtures of the present invention, it is preferred that the ratio of MI to benzoic acid is from 1/0.1 to 1/100 and more preferably from 1/0.13 to 1/67. When citric acid is used in the synergistic mixtures of the present invention, it is preferred that the ratio of MI to citric acid is from 1/8 to 1/40 and more preferably from 1/8 to 1/24. When sorbic acid is used in the synergistic mixtures of the present invention, it is preferred that the ratio of MI to sorbic acid is from 1/2 to 1/150, more preferably from 1/4 to 1/133 and most preferably from 1/4 to 1/67. When 1,2-dibromo-2,4-dicyanobutane is used in the synergistic mixtures of the present invention, it is preferred that the ratio of MI to 1,2-dibromo-2,4-dicyanobutane is from 1/0.4 to 1/100. When 1,3-dimethylol-5,5-dimethylhydantoin is used in the synergistic mixtures of the present invention, it is preferred that the ratio of MI to 1,3-dimethylol-5,5-dimethylhydantoin is from 1/0.05 to 1/100 and more preferably from 1/0.06 to 1/80. When phenoxyethanol is used in the synergistic mixtures of the present invention, it is preferred that the ratio of MI to phenoxyethanol is from 1/1 to 1/1000 and more preferably from 1/2 to 1/800. When zinc pyrithione is used in the synergistic mixtures of the present invention, it is preferred that the ratio of MI to zinc pyrithione is from 1/0.001 to 1/20 and more preferably from 1/0.0013 to 1/13. When climbazole is used in the synergistic mixtures of the present invention, it is preferred that the ratio of MI to climbazole is from 1/0.03 to 1/30 and more preferably from 1/0.05 to 1/24. When benzyl alcohol is used in the synergistic mixtures of the present invention, it is preferred that the ratio of MI benzyl alcohol is from 1/0.13 to 1/32 or from 1/80 to 1/1600 and more preferably from 1/80 to 1/400.

Some embodiments of the invention are described in detail in the following Examples. All ratios, parts and percentages are expressed by weight unless otherwise specified, and all reagents used are of good commercial quality unless otherwise specified. Abbreviations used in the Examples and Tables are listed below with the corresponding descriptions:
MI=2-methyl-3-isothiazolone
SI=synergy index
MIC=minimum inhibitory concentration

EXAMPLES

The synergism of the combinations of the present invention was demonstrated by testing a wide range of concentrations and ratios of the compounds.

Synergism was determined by an industrially accepted method described by Kull, F. C.; Eisman, P. C.; Sylwestrowicz, H. D. and Mayer, R. L., in Applied Microbiology 9:538-541 (1961), using the ratio determined by the formula:

$$Q_a/Q_A + Q_b/Q_B = \text{Synergy Index ("SI")}$$

wherein:

$Q_A$=concentration of compound A (first component) in ppm, acting alone, which produced an end point (MIC of Compound A).

$Q_a$=concentration of compound A in ppm, in the mixture, which produced an end point.

$Q_B$=concentration of compound B (second component) in ppm, acting alone, which produced an end point (MIC of Compound B).

$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides was tested by conducting high resolution MIC assays in the presence of various concentrations of MI. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient. The synergy of the combinations of the present invention was determined against two bacteria, Staphylococcus aureus (S. aureus—ATCC #6538) or Pseudomonas aeruginosa (P. aeruginosa—ATCC #9027), a yeast, Candida albicans (C. albicans—ATCC 10231), and a mold, Aspergillus niger (A. niger—ATCC 16404). The bacteria were used at a concentration of about $5\times10^6$ bacteria per mL and the yeast and mold at $5\times10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the microbicide combinations of the present invention are shown below in Tables 1 through 9. In each test, First Component (A) was MI and the Second Component (B) was the other commercial microbicide. Each table shows the specific combinations of MI and the second component; results against the microorganisms tested with incubation times; the end-point activity in ppm measured by the MIC for MI alone ($Q_A$), for the second component alone ($Q_B$), for MI in the mixture ($Q_a$) and for second component in the mixture ($Q_b$); the calculated SI value; and the range of synergistic ratios for each combination tested (MI/second component or A/B).

TABLE 1

| First Component (A) = 2-methyl-3-isothiazolone Second Component (B) = benzoic acid | | | | |
|---|---|---|---|---|
| Microorganism | $Q_a$ | $Q_b$ | SI | A/B |
| A. niger | 0 | 10000 | 1.00 | — |
| (1 week) | 50 | 10000 | 1.17 | 1/200 |
| | 200 | 10000 | 1.67 | 1/50 |
| | 300 | 0 | 1.00 | — |

TABLE 1-continued

| First Component (A) = 2-methyl-3-isothiazolone Second Component (B) = benzoic acid | | | | |
|---|---|---|---|---|
| Microorganism | $Q_a$ | $Q_b$ | SI | A/B |
| C. albicans | 0 | 5000 | 1.00 | — |
| (48 hours) | 125 | 2000 | 1.03 | 1/16 |
| | 125 | 1000 | 0.83 | 1/8 |
| | 125 | 800 | 0.79 | 1/6.4 |
| | 125 | 600 | 0.75 | 1/4.8 |
| | 125 | 500 | 0.73 | 1/4 |
| | 125 | 400 | 0.71 | 1/3.2 |
| | 125 | 300 | 0.69 | 1/2.4 |
| | 125 | 200 | 0.67 | 1/1.6 |
| | 125 | 100 | 0.65 | 1/0.8 |
| | 125 | 80 | 0.64 | 1/0.64 |
| | 125 | 60 | 0.64 | 1/0.48 |
| | 125 | 50 | 0.64 | 1/0.4 |
| | 125 | 40 | 0.63 | 1/0.32 |
| | 150 | 30 | 0.76 | 1/0.2 |
| | 150 | 20 | 0.75 | 1/0.13 |
| | 200 | 0 | 1.00 | — |
| S. aureus | 0 | 6000 | 1.00 | — |
| (72 hours) | 15 | 6000 | 1.25 | 1/400 |
| | 50 | 5000 | 1.67 | 1/100 |
| | 60 | 0 | 1.00 | — |
| P. aeruginosa | 0 | 6000 | 1.00 | — |
| (72 hours) | 15 | 2000 | 1.08 | 1/133 |
| | 15 | 1000 | 0.92 | 1/67 |
| | 15 | 800 | 0.88 | 1/53 |
| | 15 | 600 | 0.85 | 1/40 |
| | 15 | 500 | 0.83 | 1/33 |
| | 15 | 400 | 0.82 | 1/27 |
| | 15 | 300 | 0.80 | 1/20 |
| | 20 | 0 | 1.00 | — |

The synergistic ratios of MI/benzoic acid range from 1/0.13 to 1/67. The MI/benzoic acid combination showed enhanced control of Gram (−) bacteria and yeast.

TABLE 2

| First Component = 2-methyl-3-isothiazolone Second Component = citric acid | | | | |
|---|---|---|---|---|
| Microorganism | $Q_a$ | $Q_b$ | SI | A/B |
| A. niger | 0 | 10000 | 1.00 | — |
| (1 week) | 50 | 10000 | 1.17 | 1/200 |
| | 200 | 10000 | 1.67 | 1/50 |
| | 300 | 0 | 1.00 | — |
| C. albicans | 0 | 10000 | 1.00 | — |
| (72 hours) | 50 | 10000 | 1.25 | 1/200 |
| | 150 | 10000 | 1.75 | 1/67 |
| | 200 | 0 | 1.00 | — |
| S. aureus | 0 | 4000 | 1.00 | — |
| (24 hours) | 15 | 3000 | 1.13 | 1/200 |
| | 25 | 2000 | 1.13 | 1/80 |
| | 25 | 1000 | 0.88 | 1/40 |
| | 25 | 800 | 0.83 | 1/32 |
| | 25 | 600 | 0.78 | 1/24 |
| | 25 | 500 | 0.75 | 1/20 |
| | 25 | 400 | 0.73 | 1/16 |
| | 25 | 300 | 0.70 | 1/12 |
| | 25 | 200 | 0.68 | 1/8 |
| | 40 | 0 | 1.00 | — |
| P. aeruginosa | 0 | 6000 | 1.00 | — |
| (48 hours) | 2.5 | 6000 | 1.13 | 1/2400 |
| | 15 | 5000 | 1.58 | 1/333 |
| | 20 | 0 | 1.00 | — |

The synergistic ratios of MI/citric acid range from 1/8 to 1/40, preferably from 1/8 to 1/24. The MI/citric acid combinations show enhanced control of Gram (+) bacteria.

TABLE 3

| Compound A = 2-methyl-3-isothiazolone<br>Compound B = sorbic acid | | | | |
|---|---|---|---|---|
| Microorganism | $Q_a$ | $Q_b$ | SI | A/B |
| A. niger<br>(96 hours) | 0 | 4000 | 1.00 | — |
| | 50 | 3000 | 0.92 | 1/60 |
| | 75 | 3000 | 1.00 | 1/40 |
| | 75 | 2000 | 0.75 | 1/27 |
| | 100 | 3000 | 1.08 | 1/30 |
| | 100 | 2000 | 0.83 | 1/20 |
| | 125 | 3000 | 1.17 | 1/24 |
| | 125 | 2000 | 0.92 | 1/16 |
| | 125 | 1000 | 0.67 | 1/8 |
| | 150 | 2000 | 1.00 | 1/13 |
| | 150 | 1000 | 0.75 | 1/6.7 |
| | 150 | 800 | 0.70 | 1/5 |
| | 200 | 2000 | 1.17 | 1/10 |
| | 200 | 1000 | 0.92 | 1/5 |
| | 200 | 800 | 0.87 | 1/4 |
| | 300 | 0 | 1.00 | — |
| C. albicans<br>(72 hours) | 0 | 400 | 1.00 | — |
| | 50 | 400 | 1.25 | 1/8 |
| | 150 | 300 | 1.50 | 1/2 |
| | 200 | 0 | 1.00 | — |
| S. aureus<br>(72 hours) | 0 | 10000 | 1.00 | — |
| | 40 | 4000 | 1.07 | 1/100 |
| | 40 | 3000 | 0.97 | 1/75 |
| | 50 | 2000 | 1.03 | 1/40 |
| | 50 | 1000 | 0.93 | 1/20 |
| | 50 | 800 | 0.91 | 1/16 |
| | 50 | 600 | 0.89 | 1/12 |
| | 50 | 500 | 0.88 | 1/10 |
| | 50 | 400 | 0.87 | 1/8 |
| | 50 | 300 | 0.86 | 1/6 |
| | 50 | 200 | 0.85 | 1/4 |
| | 60 | 0 | 1.00 | — |
| P. aeruginosa<br>(48 hours) | 0 | 10000 | 1.00 | — |
| | 15 | 3000 | 1.05 | 1/200 |
| | 15 | 2000 | 0.95 | 1/133 |
| | 15 | 1000 | 0.85 | 1/67 |
| | 20 | 0 | 1.00 | — |

The synergistic rations of MI/sorbic acid range from 1/4 to 1/133, preferably from 1/4 to 1/67. The MI/sorbic acid combination showed enhanced control of mold and both Gram (+) and Gram (−) bacteria.

TABLE 4

| First Component = 2-methyl-3-isothiazolone<br>Second Component = 1,2-dibromo-2,4-dicyanobutane | | | | |
|---|---|---|---|---|
| Microorganism | $Q_a$ | $Q_b$ | SI | A/B |
| A. niger<br>(1 week) | 0 | 100 | 1.00 | — |
| | 50 | 100 | 1.17 | 1/2 |
| | 200 | 100 | 1.67 | 1/0.5 |
| | 300 | 0 | 1.00 | — |
| C. albicans<br>(72 hours) | 0 | 500 | 1.00 | — |
| | 125 | 200 | 1.03 | 1/1.6 |
| | 150 | 200 | 1.15 | 1/1.3 |
| | 150 | 100 | 0.95 | 1/0.7 |
| | 150 | 80 | 0.91 | 1/0.5 |
| | 150 | 60 | 0.87 | 1/0.4 |
| | 200 | 0 | 1.00 | — |
| S. aureus<br>(72 hours) | 0 | 1000 | 1.00 | — |
| | 40 | 800 | 1.47 | 1/20 |
| | 50 | 200 | 1.03 | 1/4 |
| | 50 | 100 | 0.93 | 1/2 |
| | 50 | 80 | 0.91 | 1/1.6 |
| | 60 | 0 | 1.00 | — |
| P. aeruginosa<br>(24 hours) | 0 | 800 | 1.00 | — |
| | 5 | 500 | 0.96 | 1/100 |
| | 7.5 | 400 | 1.00 | 1/53 |
| | 7.5 | 300 | 0.88 | 1/40 |
| | 10 | 300 | 1.04 | 1/30 |
| | 10 | 200 | 0.92 | 1/20 |
| | 10 | 100 | 0.79 | 1/10 |
| | 15 | 0 | 1.00 | — |

The synergistic ratios of MI/1,2-dibromo-2,4-dicyanobutane range from 1/0.4 to 1/100. The MI/1,2-dibromo-2,4-dicyanobutane combination showed enhanced control of yeast and both Gram (+) and Gram (−) bacteria.

TABLE 5

| First Component = 2-methyl-3-isothiazolone<br>Second Component = 1,3-dimethylol-5,5-dimethylhydantoin | | | | |
|---|---|---|---|---|
| Microorganism | $Q_a$ | $Q_b$ | SI | A/B |
| A. niger<br>(1 week) | 0 | 3000 | 1.00 | — |
| | 50 | 3000 | 1.17 | 1/60 |
| | 200 | 2000 | 1.33 | 1/10 |
| | 300 | 0 | 1.00 | — |
| C. albicans<br>(72 hours) | 0 | 3000 | 1.00 | — |
| | 50 | 3000 | 1.25 | 1/60 |
| | 150 | 3000 | 1.75 | 1/20 |
| | 200 | 0 | 1.00 | — |
| S. aureus<br>(72 hours) | 0 | 200 | 1.00 | — |
| | 15 | 100 | 0.75 | 1/6.7 |
| | 15 | 80 | 0.65 | 1/5.3 |
| | 15 | 60 | 0.55 | 1/4 |
| | 25 | 100 | 0.92 | 1/4 |
| | 25 | 80 | 0.82 | 1/3.2 |
| | 25 | 60 | 0.72 | 1/2.4 |
| | 25 | 50 | 0.67 | 1/2 |
| | 40 | 80 | 1.07 | 1/2 |
| | 40 | 60 | 0.97 | 1/1.5 |
| | 40 | 50 | 0.92 | 1/1.25 |
| | 40 | 40 | 0.87 | 1/1 |
| | 40 | 30 | 0.82 | 1/0.75 |
| | 50 | 40 | 1.03 | 1/0.8 |
| | 50 | 30 | 0.98 | 1/0.6 |
| | 50 | 20 | 0.93 | 1/0.4 |
| | 50 | 10 | 0.88 | 1/0.2 |
| | 50 | 5 | 0.86 | 1/0.1 |
| | 50 | 3 | 0.85 | 1/0.06 |
| | 60 | 0 | 1.00 | — |
| P. aeruginosa<br>(24 hours) | 0 | 300 | 1.00 | — |
| | 2.5 | 200 | 0.83 | 1/80 |
| | 5 | 200 | 1.00 | 1/40 |
| | 5 | 100 | 0.67 | 1/20 |
| | 5 | 80 | 0.60 | 1/16 |
| | 7.5 | 200 | 1.17 | 1/27 |
| | 7.5 | 100 | 0.83 | 1/13 |
| | 7.5 | 80 | 0.77 | 1/11 |
| | 7.5 | 60 | 0.70 | 1/8 |
| | 7.5 | 50 | 0.67 | 1/6.7 |
| | 10 | 100 | 1.00 | 1/10 |
| | 10 | 80 | 0.93 | 1/8 |
| | 10 | 60 | 0.87 | 1/6 |
| | 10 | 40 | 0.80 | 1/4 |
| | 10 | 20 | 0.73 | 1/2 |
| | 10 | 8 | 0.69 | 1/0.8 |
| | 15 | 0 | 1.00 | — |

The synergistic ratios of MI/1,3-dimethylol-5,5-dimethylhydantoin range from 1/0.06 to 1/80. The MI/1,3-dimethylol-5,5-dimethylhydantoin combination showed enhanced control of both Gram (+) and Gram (−) bacteria.

TABLE 6

| Microorganism | $Q_a$ | $Q_b$ | SI | A/B |
|---|---|---|---|---|
| First Component = 2-methyl-3-isothiazolone | | | | |
| Second Component = phenoxyethanol | | | | |
| A. niger (72 hours) | 0 | 4000 | 1.00 | — |
| | 50 | 3000 | 0.92 | 1/60 |
| | 50 | 2000 | 0.67 | 1/40 |
| | 75 | 3000 | 1.00 | 1/40 |
| | 75 | 2000 | 0.75 | 1/27 |
| | 100 | 3000 | 1.08 | 1/30 |
| | 100 | 2000 | 0.83 | 1/20 |
| | 125 | 3000 | 1.17 | 1/24 |
| | 125 | 2000 | 0.92 | 1/16 |
| | 150 | 2000 | 1.00 | 1/13 |
| | 300 | 0 | 1.00 | — |
| C. albicans (72 hours) | 0 | 4000 | 1.00 | — |
| | 50 | 3000 | 1.00 | 1/60 |
| | 75 | 3000 | 1.13 | 1/40 |
| | 75 | 2000 | 0.88 | 1/27 |
| | 100 | 2000 | 1.00 | 1/20 |
| | 125 | 2000 | 1.13 | 1/16 |
| | 125 | 1000 | 0.88 | 1/8 |
| | 125 | 800 | 0.83 | 1/6.4 |
| | 125 | 600 | 0.78 | 1/4.8 |
| | 125 | 500 | 0.75 | 1/4 |
| | 150 | 1000 | 1.00 | 1/6.7 |
| | 150 | 800 | 0.95 | 1/5.3 |
| | 150 | 600 | 0.90 | 1/4 |
| | 150 | 500 | 0.88 | 1/3.3 |
| | 150 | 300 | 0.83 | 1/2 |
| | 200 | 0 | 1.00 | — |
| S. aureus (72 hours) | 0 | 4000 | 1.00 | — |
| | 50 | 2000 | 1.13 | 1/40 |
| | 60 | 1000 | 1.00 | 1/17 |
| | 60 | 800 | 0.95 | 1/13 |
| | 80 | 0 | 1.00 | — |
| P. aeruginosa (24 hours) | 0 | 3000 | 1.00 | — |
| | 2.5 | 2000 | 0.83 | 1/800 |
| | 5 | 2000 | 1.00 | 1/400 |
| | 7.5 | 2000 | 1.17 | 1/267 |
| | 7.5 | 1000 | 0.83 | 1/133 |
| | 7.5 | 800 | 0.77 | 1/107 |
| | 7.5 | 600 | 0.70 | 1/80 |
| | 10 | 1000 | 1.00 | 1/100 |
| | 10 | 800 | 0.93 | 1/80 |
| | 10 | 600 | 0.87 | 1/60 |
| | 10 | 400 | 0.80 | 1/40 |
| | 10 | 300 | 0.77 | 1/30 |
| | 15 | 0 | 1.00 | — |

The synergistic ratios of MI/phenoxyethanol range from 1/2 to 1/800. The MI/phenoxyethanol combination showed enhanced control of Gram (+) and Gram (−) bacteria as well as yeast and mold.

TABLE 7

| Microorganism | $Q_a$ | $Q_b$ | SI | A/B |
|---|---|---|---|---|
| First Component = 2-methyl-3-isothiazolone | | | | |
| Second Component = zinc pyrithione | | | | |
| A. niger (1 week) | 0 | 80 | 1.00 | — |
| | 50 | 10 | 0.29 | 1/0.2 |
| | 75 | 60 | 1.00 | 1/0.8 |
| | 75 | 50 | 0.88 | 1/0.67 |
| | 75 | 40 | 0.75 | 1/0.53 |
| | 75 | 30 | 0.63 | 1/0.4 |
| | 75 | 20 | 0.50 | 1/0.27 |
| | 75 | 10 | 0.38 | 1/0.13 |
| | 75 | 8 | 0.35 | 1/0.1 |
| | 100 | 60 | 1.08 | 1/0.6 |
| | 100 | 50 | 0.96 | 1/0.5 |
| | 100 | 40 | 0.83 | 1/0.4 |
| | 100 | 30 | 0.71 | 1/0.3 |
| | 100 | 20 | 0.58 | 1/0.2 |
| | 100 | 10 | 0.46 | 1/0.1 |
| | 125 | 50 | 1.04 | 1/0.4 |
| | 125 | 40 | 0.92 | 1/0.32 |
| | 125 | 30 | 0.79 | 1/0.24 |
| | 125 | 20 | 0.67 | 1/0.16 |
| | 125 | 8 | 0.52 | 1/0.06 |
| | 150 | 40 | 1.00 | 1/0.27 |
| | 150 | 30 | 0.88 | 1/0.2 |
| | 150 | 20 | 0.75 | 1/0.13 |
| | 150 | 8 | 0.60 | 1/0.05 |
| | 200 | 30 | 1.04 | 1/0.15 |
| | 200 | 20 | 0.92 | 1/0.1 |
| | 200 | 10 | 0.79 | 1/0.05 |
| | 200 | 6 | 0.74 | 1/0.03 |
| | 300 | 0 | 1.00 | — |
| C. albicans (48 hours) | 0 | 80 | 1.00 | — |
| | 50 | 60 | 1.00 | 1/1.2 |
| | 50 | 50 | 0.88 | 1/1 |
| | 50 | 40 | 0.75 | 1/0.8 |
| | 75 | 50 | 1.00 | 1/0.67 |
| | 75 | 40 | 0.88 | 1/0.53 |
| | 75 | 30 | 0.75 | 1/0.4 |
| | 75 | 20 | 0.63 | 1/0.27 |
| | 75 | 8 | 0.48 | 1/0.1 |
| | 100 | 40 | 1.00 | 1/0.4 |
| | 100 | 30 | 0.88 | 1/0.3 |
| | 100 | 20 | 0.75 | 1/0.2 |
| | 100 | 10 | 0.63 | 1/0.1 |
| | 100 | 6 | 0.58 | 1/0.06 |
| | 125 | 30 | 1.00 | 1/0.24 |
| | 125 | 20 | 0.88 | 1/0.16 |
| | 125 | 10 | 0.75 | 1/0.08 |
| | 125 | 5 | 0.69 | 1/0.04 |
| | 125 | 3 | 0.66 | 1/0.024 |
| | 150 | 20 | 1.00 | 1/0.13 |
| | 150 | 10 | 0.88 | 1/0.067 |
| | 150 | 5 | 0.81 | 1/0.033 |
| | 150 | 1 | 0.76 | 1/0.0067 |
| | 150 | 0.5 | 0.76 | 1/0.0033 |
| | 150 | 0.2 | 0.75 | 1/0.0013 |
| | 200 | 0 | 1.00 | — |
| S. aureus (72 hours) | 0 | 20 | 1.00 | — |
| | 15 | 20 | 1.30 | 1/1.3 |
| | 40 | 20 | 1.80 | 1/0.5 |
| | 50 | 0 | 1.00 | — |
| P. aeruginosa (72 hours) | 0 | 200 | 1.00 | — |
| | 7.5 | 100 | 0.88 | 1/13 |
| | 10 | 100 | 1.00 | 1/10 |
| | 10 | 80 | 0.90 | 1/8 |
| | 15 | 50 | 1.00 | 1/3.3 |
| | 15 | 40 | 0.95 | 1/2.7 |
| | 15 | 30 | 0.90 | 1/2 |
| | 15 | 20 | 0.85 | 1/1.3 |
| | 15 | 10 | 0.80 | 1/0.67 |
| | 15 | 5 | 0.78 | 1/0.33 |
| | 15 | 3 | 0.77 | 1/0.2 |
| | 20 | 0 | 1.00 | — |

The synergistic ratios of MI/zinc pyrithione range from 1/0.0013 to 1/13. The MI/zinc pyrithion combination showed enhanced control of Gram (−) bacteria and both yeast and mold.

TABLE 8

| Microorganism | $Q_a$ | $Q_b$ | SI | A/B |
|---|---|---|---|---|
| First Component = 2-methyl-3-isothiazolone | | | | |
| Second Component = climbazole | | | | |
| C. albicans (72 hours) | 0 | 300 | 1.00 | — |
| | 50 | 200 | 0.92 | 1/4 |

TABLE 8-continued

First Component = 2-methyl-3-isothiazolone
Second Component = climbazole

| Microorganism | $Q_a$ | $Q_b$ | SI | A/B |
|---|---|---|---|---|
| | 75 | 200 | 1.04 | 1/2.7 |
| | 75 | 100 | 0.71 | 1/1.3 |
| | 75 | 60 | 0.58 | 1/0.8 |
| | 75 | 40 | 0.51 | 1/0.53 |
| | 100 | 200 | 1.17 | 1/2 |
| | 100 | 100 | 0.83 | 1/1 |
| | 100 | 80 | 0.77 | 1/0.8 |
| | 100 | 60 | 0.70 | 1/0.6 |
| | 100 | 40 | 0.63 | 1/0.4 |
| | 100 | 20 | 0.57 | 1/0.2 |
| | 125 | 200 | 1.29 | 1/1.6 |
| | 125 | 100 | 0.96 | 1/0.8 |
| | 125 | 80 | 0.89 | 1/0.64 |
| | 125 | 50 | 0.79 | 1/0.4 |
| | 125 | 30 | 0.73 | 1/0.24 |
| | 125 | 10 | 0.66 | 1/0.08 |
| | 150 | 80 | 1.02 | 1/0.53 |
| | 150 | 60 | 0.95 | 1/0.4 |
| | 150 | 40 | 0.88 | 1/0.27 |
| | 150 | 20 | 0.82 | 1/0.13 |
| | 150 | 8 | 0.78 | 1/0.053 |
| | 200 | 0 | 1.00 | — |
| S. aureus | 0 | 2000 | 1.00 | — |
| (24 hours) | 25 | 800 | 1.03 | 1/32 |
| | 25 | 600 | 0.93 | 1/24 |
| | 40 | 0 | 1.00 | — |

The synergistic ratios of MI/climbazole range from 1/0.05 to 1/24. The MI/climbazole combination showed enhanced control of Gram (+) bacteria and yeast.

TABLE 9

First Component = 2-methyl-3-isothiazolone
Second Component = benzyl alcohol

| Microorganism | $Q_a$ | $Q_b$ | SI | A/B |
|---|---|---|---|---|
| A. niger | 0 | 8000 | 1.00 | — |
| (72 hours) | 100 | 6000 | 1.08 | 1/60 |
| | 125 | 5000 | 1.04 | 1/40 |
| | 125 | 4000 | 0.92 | 1/32 |
| | 125 | 3000 | 0.79 | 1/24 |
| | 300 | 0 | 1.00 | — |
| C. albicans | 0 | 6000 | 1.00 | — |
| (48 hours) | 100 | 3000 | 1.00 | 1/30 |
| | 125 | 3000 | 1.13 | 1/24 |
| | 125 | 2000 | 0.96 | 1/16 |
| | 125 | 1000 | 0.79 | 1/8 |
| | 125 | 600 | 0.73 | 1/4.8 |
| | 125 | 400 | 0.69 | 1/3.2 |
| | 125 | 200 | 0.66 | 1/1.6 |
| | 125 | 80 | 0.64 | 1/0.64 |
| | 150 | 20 | 0.75 | 1/0.13 |
| | 150 | 2000 | 1.08 | 1/13 |
| | 150 | 1000 | 0.92 | 1/6.7 |
| | 150 | 800 | 0.88 | 1/5.3 |
| | 150 | 500 | 0.83 | 1/3.3 |
| | 150 | 200 | 0.78 | 1/1.3 |
| | 150 | 80 | 0.76 | 1/0.53 |
| | 150 | 40 | 0.76 | 1/0.27 |
| | 200 | 0 | 1.00 | — |
| S. aureus | 0 | 8000 | 1.00 | — |
| (72 hours) | 40 | 4000 | 1.17 | 1/100 |
| | 50 | 2000 | 1.08 | 1/40 |
| | 50 | 1000 | 0.96 | 1/20 |
| | 50 | 800 | 0.93 | 1/16 |
| | 50 | 500 | 0.90 | 1/10 |
| | 50 | 300 | 0.87 | 1/6 |
| | 50 | 100 | 0.85 | 1/2 |
| | 50 | 50 | 0.84 | 1/1 |
| | 60 | 0 | 1.00 | — |
| P. aeruginosa | 0 | 6000 | 1.00 | — |
| (24 hours) | 2.5 | 5000 | 1.00 | 1/2000 |
| | 2.5 | 4000 | 0.83 | 1/1600 |
| | 5 | 4000 | 1.00 | 1/800 |
| | 5 | 3000 | 0.83 | 1/600 |
| | 5 | 2000 | 0.67 | 1/400 |
| | 5 | 800 | 0.47 | 1/160 |
| | 7.5 | 2000 | 0.83 | 1/267 |
| | 7.5 | 1000 | 0.67 | 1/133 |
| | 7.5 | 600 | 0.60 | 1/80 |
| | 10 | 2000 | 1.00 | 1/200 |
| | 10 | 1000 | 0.83 | 1/100 |
| | 10 | 800 | 0.80 | 1/80 |
| | 10 | 500 | 0.75 | 1/50 |
| | 10 | 300 | 0.72 | 1/30 |
| | 10 | 100 | 0.68 | 1/10 |
| | 10 | 60 | 0.68 | 1/6 |
| | 15 | 0 | 1.00 | — |

The synergistic ratios of MI/benzyl alcohol range from 1/0.1 to 1/1600, preferably from 1/0.13 to 1/32 or from 1/80 to 1/1600, and more preferably from 1/80 to 1/400. The MI/benzyl alcohol combination showed enhanced control of Gram (+) and Gram (−) bacteria as well as mold and yeast.

We claim:

1. A microbicidal composition consisting of 2-methyl-3-isothiazolone and benzoic acid which is effective for inhibiting growth of *Candida albicans*; wherein a ratio of 2-methyl-3-isothiazolone to benzoic acid is from 1/0.13 to 1/8, and over such range the composition exhibits synergy for inhibiting growth of *Candida albicans*.

* * * * *

UNITED STATES PATENT AND TRADEMARK OFFICE
CERTIFICATE OF CORRECTION

PATENT NO.       : 9,034,905 B2
APPLICATION NO.  : 10/665343
DATED            : May 19, 2015
INVENTOR(S)      : Megan Anne Diehl Page 1 of 1

It is certified that error appears in the above-identified patent and that said Letters Patent is hereby corrected as shown below:

In the Claims

Column 14, Line 47, Claim 1, "a ratio" should be "the ratio"

Signed and Sealed this
Twenty-ninth Day of September, 2015

Michelle K. Lee
*Director of the United States Patent and Trademark Office*